United States Patent [19]

Hall

[11] Patent Number: 5,438,230
[45] Date of Patent: Aug. 1, 1995

[54] PIEZOELECTRIC MATERIAL DETECTOR
[75] Inventor: Dale G. Hall, Cedar Crest, N. Mex.
[73] Assignee: Motorola, Inc., Schaumburg, Ill.
[21] Appl. No.: 350,248
[22] Filed: Dec. 6, 1994

Related U.S. Application Data

[63] Continuation of Ser. No. 203,238, Feb. 28, 1994, abandoned.

[51] Int. Cl.⁶ .............................................. H01L 41/08
[52] U.S. Cl. ...................................... 310/316; 310/317; 310/318
[58] Field of Search .............................. 310/316–318, 310/330, 348; 340/617, 621

[56] References Cited

U.S. PATENT DOCUMENTS

| | | | |
|---|---|---|---|
| 3,625,058 | 12/1972 | Endress | 73/290 V |
| 3,816,773 | 6/1974 | Baldwin et al. | 310/339 |
| 4,079,362 | 3/1978 | Grimm et al. | 340/259 |
| 4,110,654 | 8/1978 | Paul | 310/323 |
| 4,314,242 | 2/1982 | Kuru | 340/316 |
| 4,319,580 | 3/1982 | Colley et al. | 128/661 |
| 4,401,909 | 8/1983 | Gorsek | 310/328 |
| 4,540,981 | 9/1985 | Lapetina et al. | 340/618 |
| 4,594,584 | 6/1986 | Pfeiffer | 340/620 |
| 4,637,403 | 1/1987 | Garcia et al. | 128/770 |
| 4,727,277 | 2/1988 | Adams | 310/323 |
| 4,785,664 | 11/1988 | Reebs | 73/290 V |
| 4,964,090 | 10/1990 | McCarthy | 367/162 |
| 4,995,402 | 2/1991 | Smith et al. | 128/771 |
| 5,142,183 | 8/1992 | Burgess | 310/339 |
| 5,191,795 | 3/1993 | Fellingharn et al. | 73/599 |

Primary Examiner—Thomas M. Dougherty
Attorney, Agent, or Firm—Gary J. Cunningham

[57] ABSTRACT

An improved piezoelectric material detector. The material detector (10) has a transducer structure (12) adapted to provide a certain vibration activity. A reset circuit (30) is included to minimize the possibility of false readings. And, a driving circuit (52) and detecting circuit (68) are utilized to drive and sense the presence of a material.

12 Claims, 2 Drawing Sheets

PIEZOELECTRIC MATERIAL DETECTOR

This is a continuation of application Ser. No. 08/203,238, filed Feb. 28, 1994, and now abandoned.

FIELD OF THE INVENTION

This invention relates to transducers, and more particularly, to an improved piezoelectric material detector.

BACKGROUND OF THE INVENTION

It is known in the art, that photographic copying machines use powder-like toner material to copy images. In many machines using toner, a particularly troublesome characteristic is the unanticipated exhaustion of the toner supply. In many of these machines, the toner is kept in a refillable cartridge or chamber into which the powder toner refills are added. When the copier runs out of toner, it must be replenished.

Handling toner material often is unpleasant and troublesome, because it can be dirty and stain anything that it comes into contact with, including clothing, skin, paper and the like. For this reason, determining the toner level in a copier without having to come into contact with it is a desirable feature.

Piezoelectric devices to sense a level of toner material in a copier have been used in the past. A piezoelectric device such as the one shown in FIG. 1, can be made to vibrate at a predetermined frequency, the vibrations of which are dampened or suppressed when the level of powder or toner is such that the powder surrounds or otherwise comes into contact with the piezoelectric vibrating element.

A problem with prior art toner level sensors 2, such as the one shown in FIG. 1, is that false indications are common because the powder material tends to cake up in proximity to the sensor 6. The sensor 6 has relatively wide protective fins 4 around the piezoelectric element 6, which quite often cause the toner material to accumulate on and around the piezoelectric element 6, even though the level of the toner in the copier's canister has dropped by its use.

Since the piezoelectric elements 6 are very sensitive and delicate devices, they are susceptible to damage during installation or other handling. For this reason, fins or veins 4 are provided to protect the piezoelectric elements from damage during both their installation and use over time. The structure and arrangement for these fins has been found to be a source of invalid toner level detection, because of the accumulation of toner material between the fins 4 and the piezoelectric element 6.

A piezoelectric based material sensor that avoids the problems of toner accumulation on or around the piezoelectric element and minimizes false readings, would be an improvement over the art.

DETAILED DESCRIPTION OF THE PREFERRED EMBODIMENT

Figure 2:
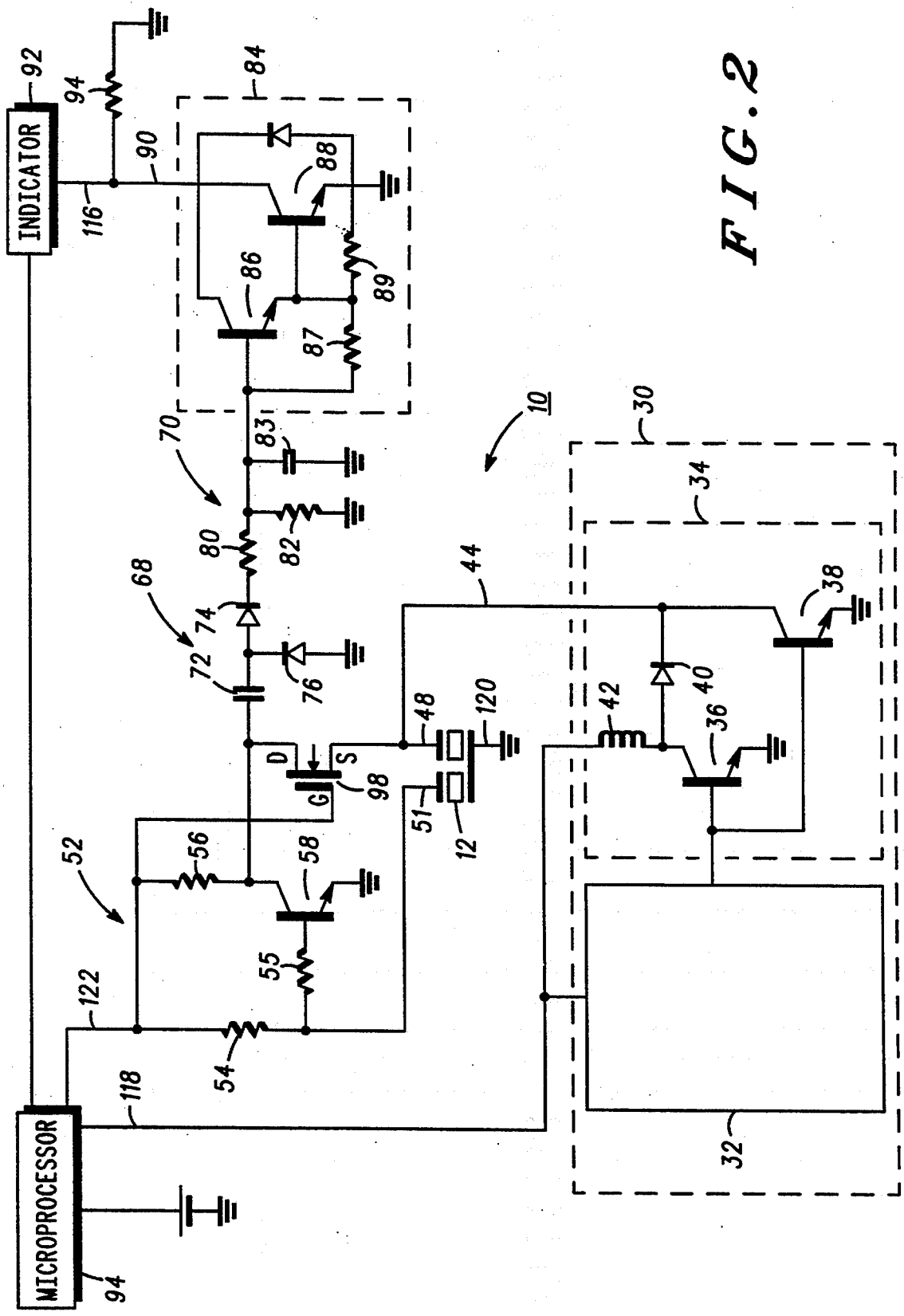
FIG. 2 shows a representative schematic diagram of an improved piezoelectric material detector in accordance with the present invention.

FIG. 2 provides a schematic diagram of an improved piezoelectric material detector 10. It is particularly adapted for use in connection with photocopying machines and the like, which use powder material, such as toner stored in a reservoir for eventual use. Alternatively, the detector 10 can be used and has application in detecting powdered materials, aggregates, sand, flour, liquids and other substances and materials, as should be understood by those skilled in the art.

The material detector 10, includes a transducer structure 12 for providing a predetermined vibration activity; a reset circuit 30 for minimizing false readings coupled to the transducer structure 12; a driver 50 for causing the transducer structure 12 to vibrate, coupled to the transducer; and a detector 68 for detecting a predetermined threshold vibration activity below which is indicative of a presence of a material, coupled to the transducer structure 12, whereby the presence or absence of a material is determinable.

In a preferred embodiment, the oscillator IC 32 is a dual timer integrated circuit with suitable components, such as capacitors and resistors, etc. providing an output signal sweeping from 2–4 kHz, to excite a natural resonance of the transducer structure 12. The oscillator IC 32 is part number MC3456, and is available from Motorola.

Figure 1:
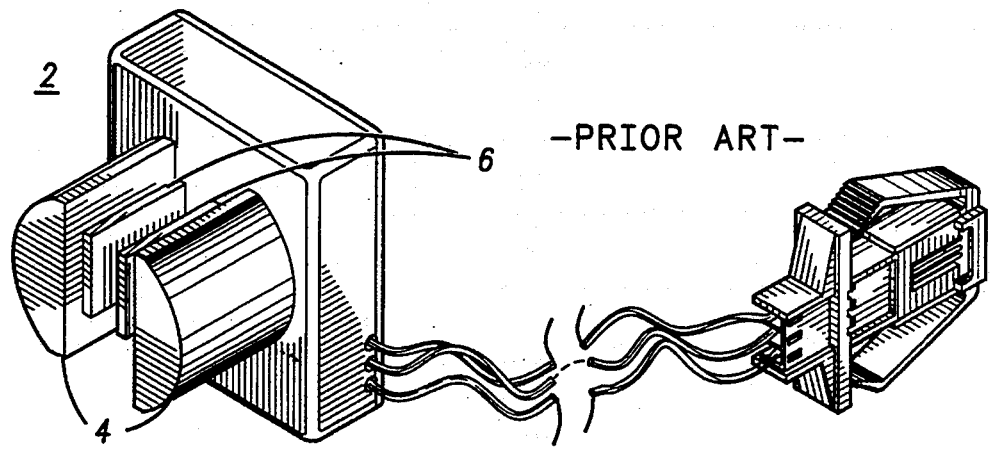
FIG. 1 shows a perspective view of a prior art piezoelectric toner sensor.
Figure 3:
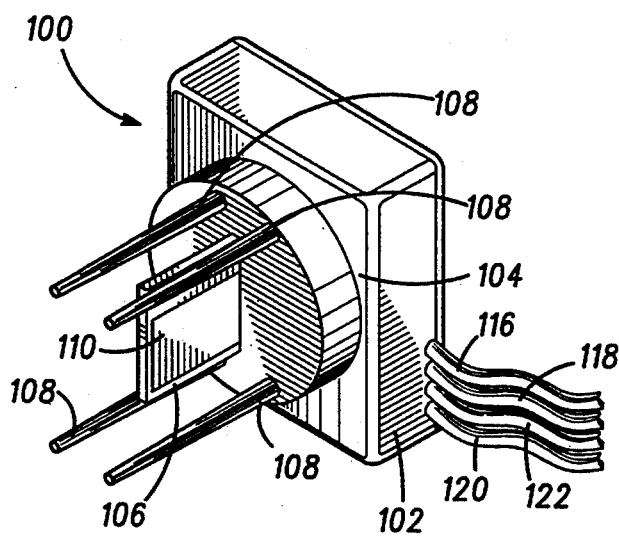
FIG. 3 shows a perspective view of an improved transducer structure in accordance with the present invention.
Figure 4:
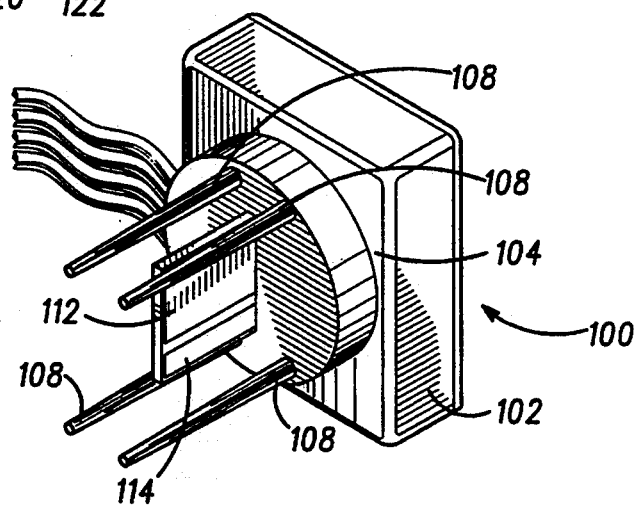
FIG. 4 shows a perspective view of the transducer structure in FIG. 3 rotated 180°, in accordance with the present invention.

More particularly, the driver 50 can include an oscillator used to excite or modulate the transducer structure 12. The oscillator circuit 52 comprises resistors 54, 55 and 56, and transistor 58. The oscillator circuit 52 will nominally oscillate a cantilevered transducer or piezoelectric element, as shown in FIGS. 3 and 4, at 2300 Hz in free air. The frequency and displacement of the transducer will be affected by the presence of solid particles in contact with a portion of the transducer structure 12 (probe 100 in FIGS. 3 and 4).

The detector circuit 68 in FIG. 2 includes a capacitor 72 and first and second diodes 74 and 76 for providing filtering and rectification of the oscillating signal. The detector circuit 68 provides a voltage that switches the open collector transistor at an output port 90.

A third resistor 80, fourth resistor 82 and capacitor 83 define a noise filter 70 for filtering the output of the detector circuit 68. The filtered signal from filter 70 provides a substantially DC voltage to the Darlington pair 84. The Darlington pair 84 includes transistors 86 and 88, resistors 87 and 89 and an output line 90. The output line 90 can be coupled to a suitable indicator 92. The indicator could be a volt meter, CRT monitor, or the like, for suitably indicating whether or not the material detector detected material, indicating that the reservoir is full or empty, respectively. The resistor 94 is a pull up resistor, for example, which can be utilized to determine whether the vibrations of the transducer structure 12 have been dampened by the presence of powder (or other similar materials) in contact with the transducer structure 12.

In one application, a container is filled with a material, such as a toner powder, and a portion of the transducer structure 12 is suitably inserted into the container. If the container is substantially filled with material, the vibration of the transducer structure 12 will be dampened, and the signal at output line 90 will be at a predetermined level indicating the presence of a powder. Thus, the container does not need to be filled. Alternatively, when a portion (probe 100) of the transducer structure 12 does not have material in proximity thereto, the output line 90 will have a predetermined signal, such as a low signal. This signal is fed to the indicator 92 so that a user will be alerted to the need to fill the container or reservoir with powder, for example.

As should be understood by those skilled in the art, the reset circuit 30 and oscillator circuit 52, can each be suitably switched on and off independently by any appropriate switching devices.

In a preferred embodiment, a microprocessor 98 suitably cycles the reset circuit 30 on for a predetermined period and thereafter suitably switches the detector circuit 68 on for a predetermined period of time for improved accuracy and minimizing false readings. More particularly, when the reset circuit 30 is cycled on a predetermined DC signal is connected to the oscillator IC 32, through line 118, to vigorously vibrate, clear and reset probe 100 for a predetermined period of time, such as about 5 seconds. Thereafter, the reset circuit 30 is shut off and the detector circuit 68 is actuated.

In the reset mode, the microprocessor switches off power to the oscillator 52 as well as the gate of the FET 98. The FET 98 switches to a high impedance state effectively blocking current from the reset circuit 30 connected at the FET source to the detector circuit 68 connected at the FET drain, that could damage the Darlington pair 84. During reset, the oscillator 32 switches transistor 36 so that DC current through coil 42 is chopped and the voltage rises as the field collapses pumping current at a high voltage through line 44 to the transducer input 48. The frequency of the oscillator 32 is swept through resonance causing vigorous motion that shakes off caked powder in proximity to probe 100.

After the reset circuit is shut off, the microprocessor applies a DC voltage to the oscillator circuit 52 through line 122, and current passes to the gate of the FET 98, switching it to a low impedance state. Current can now pass through resistor 56 to the FET drain, to the source, and to the transducer input 48 of the transducer structure 12. If there is no powder present around the transducer structure 12, it will readily bend due to the piezoelectric effect. This bending is sensed at the feed back electrode 51 by virtue of the reciprocal nature of piezoelectric. The feedback current can be made to be out of phase with the driver current. It is fed to the base of transistor 58 through resistor 55, causing the transistor 58 to conduct, and pulling down the collector voltage and reducing the current flow to the transducer input 48. This causes the transducer structure 12 to bend back toward the straight position. Inertia causes the transducer structure 12 to continue past the neutral position, which reverses the feedback current. Since the gain of the transistor 58 is greater than one, the circuit 52 oscillates at the natural cantilever frequency of the transducer structure 12. This oscillation produces an AC current that passes through capacitor 72, and is doubled and rectified by diodes 74 and 76, to allow DC current to pass through filter circuit 70, and Darlington pair 84. The resistor 94 pulls down the voltage at line 90, which indicates a low powder situation. When powder is present, the oscillation is dampened or prevented from starting so there is no AC current through capacitor 72, and no DC current to the base of Darlington 84, so the Darlington stops conducting and the voltage at line 90 is pulled up through the resistor 94, indicating powder is present.

FIGS. 3 and 4 show perspective views of the probe 100 for detecting the presence of materials. The probe 100 is a component of the transducer structure 12. The probe 100 can be used for detecting the level of powdered toner in a photocopier or the like. This probe 100 also finds application in detecting other materials, such as sand, aggregates, food, liquid and the like.

The probe 100 has a base 102 that has at least a substantially planar top surface 104 from which a piezoelectric element extends and suitably projects into a container or reservoir holding the powder, the presence or absence of which is to be detected.

The piezoelectric element 106 is a lead-zirconite-titanate material. The piezoelectric element 106 comprises two substantially planar piezoelectric (or ceramic) element layers bonded to opposing surfaces of a planar brass center vein. Electrodes are bonded to the opposing planar surfaces. The piezoelectric material is polarized during its fabrication. When the polarization of the piezoelectric elements is properly accomplished, an electric field with a predetermined polarity impressed upon the electrodes and the brass center vein can cause the piezoelectric layers to deflect from side to side or upwardly and downwardly depending on the orientation of the field. In the figures shown, the piezoelectric layers deflect from side to side.

The piezoelectric element 106 is mounted to the base 102 and has a length extending from the top surface 104, the length of which is determined by the desired dimensions required. Surrounding the piezoelectric element 106 are a plurality of substantially columnar protective posts 108, each of which has a length that is preferably at least as long as the piezoelectric element 106. Each of these columnar protective posts 108, extends substantially orthogonally from the top surface 104 out the base 102, and are located at predetermined locations away from the piezoelectric element 106 so as to minimize the accumulation or caking of a material in proximity to the piezoelectric element 106 and any of the posts 108. Using columnar protective posts 108, contributes to preventing the accumulation of powdered material in and around the piezoelectric element 106. In one embodiment, the base 102 is constructed of a molded plastic, which is formed at the same time with the protective posts 108. It should be understood by those skilled in the art, that various modifications to the posts can be made without departing from the novel spirit and scope of this invention.

The piezoelectric element 106 has a first electrode 110 on one side and a second electrode 112 and feedback electrode 114 on the other, and connection lines 116, 118, 120 and 122. The line 116 is coupled to the output line 90 of the Darlington pair 84. The lines 118 and 122 provide DC supply voltages to the reset circuit 30 and detector circuit 68, respectively, switchable from the microprocessor 94. And, the line 120 is simply coupled to a common ground, in FIG. 2.

Advantageously, in a preferred embodiment, most of the circuit in FIG. 2 can be enclosed in the probe 100 housing itself, with the exception of the microprocessor 94 and indicator 92. However, it should be understood that in other embodiments it may be desirable to fully enclose all of the component parts (or circuitry) or conversely, keep the circuitry and probe 100 separated.

Although the present invention has been described with reference to certain preferred embodiments, numerous modifications and variations can be made by those skilled in the art, without departing from the novel spirit and scope of this invention.

What is claimed is:

1. An improved piezoelectric material detector, comprising:
   (a) a transducer structure including a probe for providing a predetermined vibration activity;
   (b) a reset circuit for minimizing false readings coupled to the transducer structure, the reset circuit including an oscillator which sweeps through a predetermined frequency range which includes a resonant frequency of the transducer, whereby when the resonant frequency is reached, the probe is vigorously vibrated to substantially clear caked or undesirable material in proximity to the probe;
   (c) means for driving a transducer structure and detecting the presence of a material, coupled to the transducer structure; and
   (d) a switching device for actuating the reset circuit and the driving and detecting means for a predetermined time, defining (i) a reset mode whereby the probe is vibrated vigorously to substantially clear caked or undesirable material in proximity of the probe, thereby minimizing the possibility of false or inaccurate detection of the presence of a material in proximity thereto, and (ii) a detecting mode whereby the presence or absence of the material is detected, respectively.

2. The material detector of claim 1, wherein the reset means includes an oscillator and voltage multiplier in series.

3. The material detector of claim 1, wherein the driving and detecting means includes an oscillator circuit.

4. The material detector of claim 1, wherein the driving and detecting means includes a detector circuit and a noise filter circuit in series, having an output coupled to an indicator.

5. The material detector of claim 1, wherein the transducer structure includes a probe, including:
   a base having a substantially planer top surface;
   a piezoelectric element mounted to the base and having a length extending from the top surface of the base; and
   a plurality of substantially columnar protective posts, each having a length and a narrow cross-section for minimizing unwanted accumulation of material, and extending orthogonally from the planar top surface of the base, the posts being located at predetermined locations away from the piezoelectric element.

6. The material detector of claim 5, wherein the base and the protective posts are a molded plastic, and wherein the protective posts each have a length substantially equal to the length of the piezoelectric element.

7. An improved piezoelectric material detector, comprising:
   (a) a transducer structure including a probe for providing a predetermined vibration activity;
   (b) a reset circuit for minimizing false readings coupled to the transducer structure, the reset circuit including an oscillator which sweeps through a predetermined frequency range which includes a resonant frequency of the transducer, whereby when the resonant frequency is reached, the probe is vigorously vibrated to substantially clear caked or undesirable material in proximity to the probe;
   (c) a driver circuit for driving a portion of the transducer structure to vibrate, coupled to the transducer structure;
   (d) a detecting circuit for sensing the presence of a material, coupled to the transducer structure; and
   (e) a switching device for actuating the reset circuit and the driver and detecting circuits for a predetermined time, defining (i) a reset mode whereby the probe is vibrated vigorously to substantially clear caked or undesirable material in proximity of the probe, thereby minimizing the possibility of false or inaccurate detection of the presence of a material in proximity to the probe, and (ii) a detecting mode whereby the presence or absence of the material is detected, respectively.

8. The material detector of claim 7, wherein the reset circuit includes an oscillator and voltage multiplier in series.

9. The material detector of claim 7, wherein the driver circuit includes an oscillator circuit.

10. The material detector of claim 7, wherein the detector circuit is coupled to a noise filter having an output coupled to an indicator.

11. The material detector of claim 7, wherein the transducer structure includes a probe, including:
    a base having a substantially planar top surface,
    a piezoelectric element mounted to the base and having a length extending from the top surface of the base; and
    a plurality of substantially columnar protective posts, each having a length and narrow cross-section for minimizing unwanted accumulation of material, and extending orthogonally from the planar top surface of the base, the posts being located at predetermined locations away from the piezoelectric element.

12. The material detector of claim 11, wherein the base and the protective posts are a molded plastic, and wherein the protective posts each have a length substantially equal to the length of the piezoelectric element.

* * * * *